United States Patent [19]

Reizlein et al.

[11] Patent Number: 5,369,118
[45] Date of Patent: * Nov. 29, 1994

[54] N-ALKYL-LACTAMS AS CRYSTALLIZATION INHIBITORS

[75] Inventors: Karl Reizlein, Cologne; Ulrich Engelhardt, Leverkusen; Heinz-Otto Horstmann, Bergisch-Gladbach; Rolf-Jürgen Singer, Wuppertal; Klaus Wangermann, Krefeld; Wolfgang Wirth, Hennef, all of Germany

[73] Assignee: Bayer Aktiengesellschaft, Leverkusen, Germany

[*] Notice: The portion of the term of this patent subsequent to Mar. 29, 2009 has been disclaimed.

[21] Appl. No.: 502,369

[22] Filed: Mar. 30, 1990

[30] Foreign Application Priority Data

Apr. 5, 1989 [DE] Germany .................. 3910921

[51] Int. Cl.⁵ .................. A01N 43/64; C07D 249/14; C07D 249/16
[52] U.S. Cl. .................. 514/383; 548/267.8; 548/268.2
[58] Field of Search .................. 514/383; 548/268.2, 548/267.8

[56] References Cited

U.S. PATENT DOCUMENTS

| | | | |
|---|---|---|---|
| 3,952,002 | 4/1976 | Kramer et al. | 424/269 |
| 4,348,385 | 9/1982 | Synek | 424/173 |
| 4,723,984 | 2/1988 | Holmwood et al. | 71/76 |
| 4,933,337 | 6/1990 | Brandes et al. | 514/231.2 |

FOREIGN PATENT DOCUMENTS

| | | |
|---|---|---|
| 0052424 | 5/1982 | European Pat. Off. |
| 0077078 | 4/1983 | European Pat. Off. |
| 0160111 | 11/1985 | European Pat. Off. |
| 8800184 | 1/1988 | WIPO |

Primary Examiner—Allen J. Robinson
Attorney, Agent, or Firm—Sprung Horn Kramer & Woods

[57] ABSTRACT

In the spraying of an aqueous liquor comprising at least one of 1-(4-chlorophenyl)-4,4-dimethyl-3-(1,2,4-triazol-1-yl-methyl)-pentan-3-ol and 1-(4-chlorophenoxy)-3,3-dimethyl-1-(1,2,4-triazol-1-yl)-butan-2-ol, the improvement which comprises including in the liquor an N-alkyl-lactam of the formula

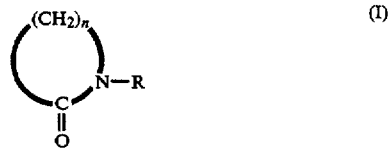

in which
R represents alkyl having 8 to 18 carbon atoms and
n represents the numbers 3, 4 or 5,

10 Claims, 2 Drawing Sheets

N-ALKYL-LACTAMS AS CRYSTALLIZATION INHIBITORS

The present invention relates to the new use of N-alkyl-lactams for preventing crystallization during application of aqueous spray liquors based on certain fungicidal active compounds.

Spray apparatuses which are usually employed for applying aqueous formulations of plant treatment agents contain several filters and nozzles. Thus, for example, there are suction filters between the suction component and tank pump, and furthermore pressure filters positioned in the pressure region downstream of the pump. Nozzle filters can also be present directly before the spray nozzles. All of these filters and the nozzles may be blocked to a greater or lesser extent by active compound which crystallizes out during application of aqueous spray liquors based on solid active compounds.

It has already been disclosed that 1-(4-chlorophenyl)-4,4-dimethyl-3-(1,2,4-triazol-1-yl-methyl)-pentan-3-ol and 1-(4-chlorophenoxy)-3,3-dimethyl-1-(1,2,4-triazol-1-yl)-butan-2-ol have a fungicidal action and can be applied in the form of aqueous spray liquors to plants and/or their environment (compare EP-OS (European Published Specification) 0,040,345 and German Patent Specification 2,324,010). Surface-active substances, such as, for example, alkylaryl polyglycol ethers, can be employed for the preparation of such spray liquors. However, a disadvantage of using these conventional formulations is that the active compounds tend to crystallize and can block both filters and nozzles of the spray apparatuses.

It has now been found that N-alkyl-lactams of the formula 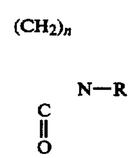 (I)

in which

R represents alkyl having 8 to 18 carbon atoms and n represents the numbers 3, 4 or 5, can be used during application of aqueous spray liquors containing A) 1-(4-chlorophenyl)-4,4-dimethyl-3-(1,2,4-triazol-1-yl-methyl)-pentan-3-ol of the formula 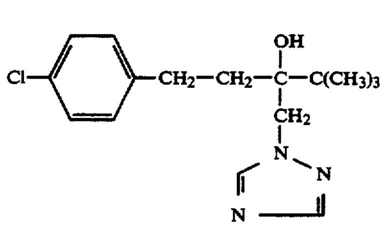 (II)

and/or 1-(4-chlorophenoxy)-3,3-dimethyl-1-(1,2,4-triazol-1-yl)-butan-2-ol of the formula 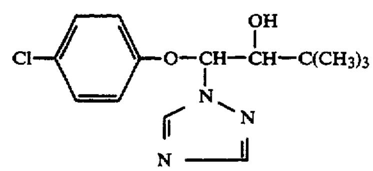 (III)

and

B) if appropriate one or more other active compounds and additives, for preventing crystallization of the active compounds of the formulae (II) and/or (III).

It is to be described as exceptionally surprising that the tendency of 1-(4-chlorophenyl)-4,4-dimethyl-3-(1,2,4-triazol-1-yl-methyl)-pentan-3-ol and 1-(4-chlorophenoxy)-3,3-dimethyl-1-(1,2,4-triazol-1-yl)-butan-2-ol to crystallize can be greatly reduced by the use according to the invention of N-alkyl-lactams of the formula (I). Above all, it was not to be expected that N-alkyllactams of the formula (I) are considerably more suitable for the purpose stated than other substances of a comparable action.

The use of N-alkyl-lactams of the formula (I) in aqueous formulations based on the fungicidal active compounds of the formulae (II) and/or (III) has a number of advantages. Thus, the N-alkyl-lactams of the formula (I) are substances which can be handled without problems and are also available in relatively large amounts. Furthermore, the use of the substances of the formula (I) prevents blocking of both the filters and the nozzles of the spray apparatuses on spraying aqueous formulations containing active compounds of the formulae (II) and/or (III). It is also advantageous that N-alkyl-lactams of the formula (I) display no undesirable side effects at all in plant protection.

Formula (I) provides a general definition of the N-alkyl-lactams which can be used according to the invention. Substances of the formula (I) which can preferably be used are those in which R represents alkyl having 8 to 14 carbon atoms and n represents the numbers 3, 4 or 5.

Substances of the formula (I) which can particularly preferably be used are those in which R represents alkyl having 8, 10 or 12 carbon atoms and n represents the numbers 3, 4 or 5.

Examples which may be mentioned of N-alkyl-lactams of the formula (I) are:

N-dodecyl-caprolactam
N-decyl-caprolactam
N-octyl-caprolactam
N-dodecyl-pyrrolidone
N-decyl-pyrrolidone
N-octyl-pyrrolidone
N-dodecyl-valerolactam
N-decyl-valerolactam
N-octyl-valerolactam.

The N-alkyl-lactams of the formula (I) are already known (compare J. Org. Chem. 18, 1087 (1953); Ann. Chem. 596, 203 (1955); J. Amer. Chem. Soc. 69, 715 (1947); DE-AS (German Published Specification) 1,160,268; EP-OS (European Published Specification) 0,077,078 and WO 88/00,184).

The active compounds of the formulae (II) and (III) and their use for combating phytopathogenic fungi are likewise known (compare EP-OS (European Published Specification) 0,040,345 and German Patent Specification 2,324,010). The active compounds can be employed here in the customary formulations. They are preferably applied in the form of aqueous spray liquors.

In addition to the active compounds of the formulae (II) and (III), the spray liquors which can be used according to the invention can also contain one or more other active compounds. Compounds which are preferably suitable here are those with fungicidal properties. Examples which may be mentioned of such active compounds which can additionally be used are:

1-(4-chlorophenoxy)-3,3-dimethyl-(1,2,4-triazol-1-yl)butan-2-one (triadimefon),
1-(4-phenyl-phenoxy)-3,3-dimethyl-(1,2,4-triazol-1-yl)butan-2-ol (bitertanol),
N,N-dimethyl-N'-phenyl-(N'-fluorodichloro-methylthio)sulphamide (dichlofluanid),
N,N-dimethyl-(N'-fluorodichloromethylthio)-N'-(4-methylphenyl)-sulphamide (tolylfluanid),
N-trichloromethylmercapto-4-cyclohexene-1,2-dicarboxamide (captan),
N-(1,1,2,2-tetrachloroethyl-sulphenyl)-cis-4-cyclohexene-1,2-dicarboxamide (captafol),
N-trichloromethylthio-phthalimide (folpet),
n-dodecyl-guanidine acetate (dodine),
tetrachloro-isophthalo-dinitrile (chlorothalonil),
4,5,6,7-tetrachlorophthalide,
zinc ethylene-bis-dithiocarbamate (zineb),
manganese ethylene-bis-dithiocarbamate (maneb),
zinc ethylene-bis-dithiocarbamate/manganese ethylene-bisdithiocarbamate (mancozeb),
zinc propylene-1,2-bis-dithiocarbamate (propineb),
1-[3-(4-(1,1-dimethylethyl)-phenyl)-2-methylpropyl]-piperidine (fenpropidin),
N-tridecyl-2,6-dimethyl-morpholine (tridemorph),
2-[2-(2,4-dichlorophenyl)-2-(2-propenyloxy)-ethyl]imidazole (imazalil),
N-[2-(2,4,6-trichlorophenoxy)-ethyl]-N-propyl-1H-imidazole (prochloraz),
1,2-dimethyl-cyclopropane-1,2-dicarboxylic acid 3,5-dichlorophenylimide (procymidone),
2-methoxycarbamoyl-benzimidazole (carbendazim),
methyl 1-(butylcarbamoyl)-2-benzimidazole-carbamate (benomyl),
2,4-dichloro-6-(2'-chlorophenyl-amino)-1,3,4-triazine (anilazine),
bis-(8-guanidine-O-octyl)-amine triacetate (guazatine),
1-(4-chlorobenzyl)-1-cyclopentyl-3-phenyl-urea (pencyron).

Possible additives which can be present in the spray liquors which can be used according to the invention are surface-active substances, organic diluents, low temperature stabilizers and adhesives.

Possible surface-active substances here are nonionic and anionic emulsifiers, such as polyoxyethylene fatty acid esters, polyoxyethylene fatty alcohol ethers, alkylaryl polyglycol ethers, alkylsulphonates, alkylsulphates and arylsulphonates. The emulsifiers may be present individually or as a mixture. Preferably mentioned are
polyoxyethylene sorbitan monolaurate having on average 20 oxyethylene units per molecule,
polyoxyethylene sorbitan monopalmitate having on average 20 oxyethylene units per molecule,
polyoxyethylene sorbitan monostearate having on average 20 oxyethylene units per molecule,
sorbitan monolaurate,
sorbitan monopalmitate,
sorbitan monostearate,
polyoxyethylene oleyl ether having on average 10 oxyethylene units per molecule,
polyoxyethylene oleyl ether having on average 20 oxyethylene units per molecule,
bis-[α-methyl-(4-methyl-benzyl)]-phenyl-polyglycol ether having on average 27 oxyethylene units per molecule,
bis-[α-methyl-(4-n-dodecyl)]-phenyl-polyglycol ether having on average 27 oxyethylene units per molecule,
bis-(4-methyl-benzyl)-phenyl-polyglycol ether having on average 27 oxyethylene units per molecule,
bis-(4-n-dodecyl-benzyl)-phenyl-polyglycol ether having on average 27 oxyethylene units per molecule,
tris-[α-methyl-(4-methyl-benzyl)]-phenyl-polyglycol ether having on average 17 oxyethylene units per molecule, nonylphenol-polyglycol ether having on average 15 oxyethylene units per molecule,
nonylphenol-diglycol ether having on average 2 oxyethylene units per molecule,
sodium n-dodecyl sulphonate,
sodium lauryl sulphate,
sodium 4-(n-nonyl)phenyl-sulphonate,
sodium 4-(tetrapropylene)-phenyl-sulphonate,
ammonium 4-(i-dodecyl)-phenyl-sulphonate,
calcium 4-(i-dodecyl)-phenyl-sulphonate,
(2-hydroxyethyl)-ammonium 4-(n-dodecyl)-phenyl-sulphonate,
bis-(2-hydroxyethyl)-ammonium 4-(n-dodecyl)-phenyl-sulphonate,
tris-(2-hydroxyethyl)-ammonium 4-(n-dodecyl)-phenyl-sulphonate,
calcium 4-(n-dodecyl)-phenyl-sulphonate.

The emulsifiers used in practice from the group of alkylaryl polyglycol ethers are in general mixtures of several compounds. These are, in particular, mixtures of substances which differ in the degree of substitution on the phenyl ring bonded to the oxyethylene unit and the number of oxyethylene units. Fractions can therefore also be calculated as mean values for the number of substituents on the phenyl ring. Examples which may be mentioned are substances for which the following average compositions result:

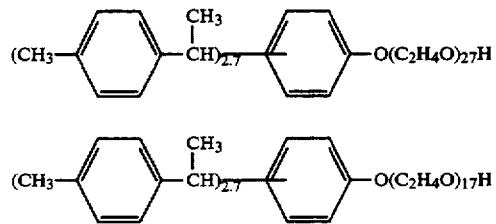

Organic diluents which can be present in the spray liquors which can be used according to the invention are all the polar and non-polar organic solvents which can be customarily employed for such purposes. Preferred possible solvents are ketones, such as methyl isobutyl ketone and cyclohexanone, and furthermore amides, such as dimethylformamide, and moreover cyclic compounds, such as N-methyl-pyrrolidone and butyrolactone, and moreover strongly polar solvents, such as dimethyl sulphoxide, and furthermore aromatic hydrocarbons, such as xylene, and in addition esters, such as propylene glycol monomethyl ether-acetate, dibutyl adipate, hexyl acetate, heptyl acetate, tri-n-butyl citrate and di-n-butyl phthalate, and furthermore alcohols, such as ethanol, n- and i-propanol, n- and i-butanol, n- and i-amyl alcohol, benzyl alcohol and 1-methoxy-2-propanol.

Low temperature stabilizers which the spray liquors which can be used according to the invention can contain are all the substances usually suitable for this purpose. Preferred possible substances are urea, glycerol and propylene glycol.

Adhesives which can be employed in the spray liquors which can be used according to the invention are all the substances which are usually suitable for this purpose. Preferred possible substances are adhesives such as carboxymethylcellulose, naturally occurring and synthetic pulverulent, granular or latex polymers, such as gum arabic, polyvinyl alcohol and polyvinyl acetate, and naturally occurring phospholipids, such as cephalins and lecithins, and also synthetic phospholipids. Further additives can be mineral and vegetable oils.

Water is moreover in each case present in the spray liquors which can be used according to the invention.

In the case of the use according to the invention of N-alkyl-lactams of the formula (I), one or more of these N-alkyl-lactams can be employed in the spray liquors.

The active compound concentrations in the spray liquors which can be used according to the invention can be varied within a certain range. The active compound concentrations are in general between 0.0001 and 3 per cent by weight, preferably between 0.001 and 2 per cent by weight.

The ratio of active compound to N-alkyl-lactam of the formula (I) can also be varied within a certain range. The weight ratio of active compound from group (A) to N-alkyl-lactam of the formula (I) is in general between 1:0.2 and 1:5, preferably between 1:0.6 and 1:2.

The amounts of other active compounds or additives in the spray liquors which can be used according to the invention can be varied within a substantial range. They are of the order of magnitude as is usually the case in such aqueous spray liquors.

The spray liquors which can be used according to the invention are prepared by customary methods. In general, a procedure is followed in which a concentrate is first prepared by bringing together the required components in any desired sequence and mixing them homogeneously at temperatures between 15° and 30° C. and if appropriate filtering the mixture formed. To prepare the ready-to-use spray liquors, the concentrated formulation is mixed with the particular desired amount of water, if appropriate with stirring and/or pumping, so that the formulation is uniformly distributed in the water as a fine dispersion.

It is also possible to add the one or more N-alkyl-lactams of the formula (I) if the concentrate is diluted with water to give the ready-to-use spray liquor.

It is possible to use, both for the preparation of the concentrated formulations and for the preparation and application of the spray liquors which can be used according to the invention, all the mixing apparatuses and spray apparatuses usually suitable for these purposes.

By using one or more N-alkyl-lactams of the formula (I) in aqueous spray liquors based on active compounds of the formulae (II) and/or (III), crystallization of the active compound both in the concentrated commercially available formulation and in the filters and discharge openings of the spray apparatuses during application of the aqueous spray liquors prepared therefrom is either completely suppressed or prevented to the extent that application of the spray liquors is not impaired.

The invention will also be described with reference to the accompanying drawings, wherein:

FIG. 1 is a photomicrograph showing crystal deposit in accordance with the prior art; and FIG. 2 to 4 are photomicrographs showing reduced crystal deposits in accordance with the invention.

The preparation and crystallization properties of the spray liquors which can be used according to the invention are illustrated by the following examples.

PREPARATION EXAMPLES

EXAMPLE 1

To prepare a formulation, 12.5 parts by weight of 1-(4-chlorophenyl)-4,4-dimethyl-3-(1,2,4-triazol-1-yl-methyl)-pentan-3-ol of the formula

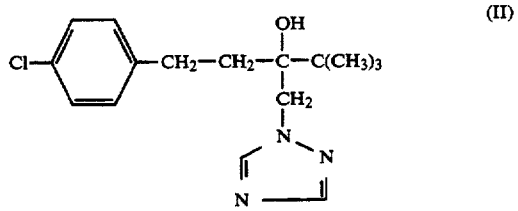

10.0 parts by weight of N-(n-dodecyl)-caprolactam,
35.0 parts by weight of cyclohexanone,
6.5 parts by weight of the em

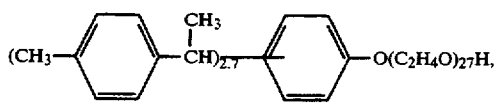

6.5 parts by weight of (2-hydroxyethyl)-ammonium 4-(n-dodecyl)-phenylsulphonate and
27.0 parts of water, are mixed at room temperature and stirred to give a homogeneous liquid. A spray liquor containing the concentrate in a concentration of 2% by weight is prepared from the resulting concentrate by mixing with water.

EXAMPLE 3

To prepare a formulation,
12.5 parts by weight of 1-(4-chlorophenyl)-4,4-dimethyl3-(1,2,4-triazol-1-yl-methyl)-pentan-3-ol of the formula

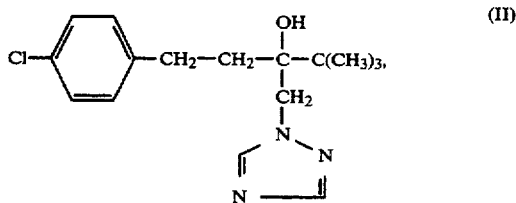

(II)

12.5 parts by weight of N-(n-dodecyl)-pyrrolidone,
36.0 parts by weight of cyclohexanone,
6.5 parts by weight of the emulsifier of the average composition of the formula

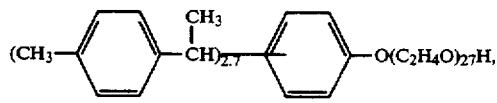

6.5 parts by weight of (2-hydroxyethyl)-ammonium 4-(n-dodecyl)-phenylsulphonate and
27.0 parts of water, are mixed at room temperature and stirred to give a homogeneous liquid. A spray liquor containing the concentrate in a concentration of 2% by weight is prepared from the resulting concentrate by mixing with water.

COMPARISON EXAMPLE A

To prepare a formulation,
12.5 parts by weight of 1-(4-chlorophenyl)-4,4-dimethyl-3-(1,2,4-triazol-1-yl-methyl)-pentan-3-ol of the formula

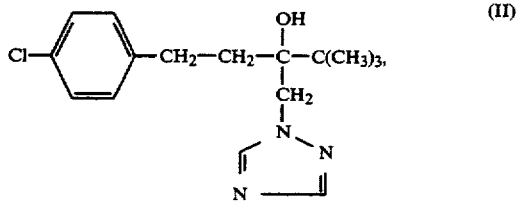

(II)

6.5 parts by weight of the emulsifier of the average composition of the formula

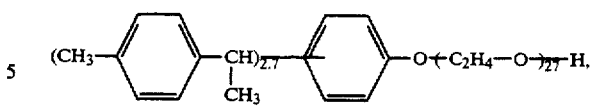

6.5 parts by weight of (2-hydroxyethyl)-ammonium 4-(n-dodecyl)-phenylsulphonate,
35.0 parts by weight of cyclohexanone and
39.5 parts by weight of water, are mixed at room temperature and stirred to give a homogeneous liquid. A spray liquor containing the concentrate in a concentration of 2% by weight is prepared from the resulting concentrate by mixing with water.

Use Example I

To test the crystallization properties, in each case 250 ml of an aqueous spray liquor having a concentrate content of 2% by weight are pumped in circulation through a fine-meshed sieve for 15 minutes in a flow-through apparatus with the aid of a pump. After this operation has been repeated eight times with 250 ml of freshly employed spray liquor each time, the crystal deposit on the sieve is photographed.

The corresponding photographs are shown in FIGS. 1 to 4.

Figure 1:
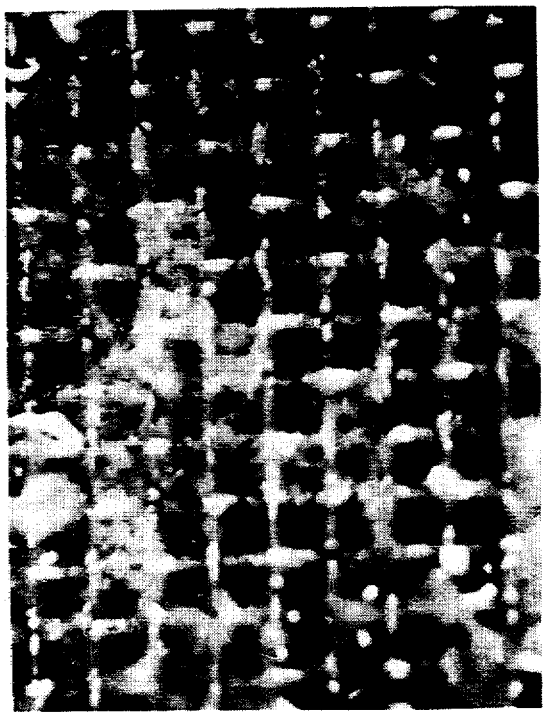
FIG. 1 shows, in 25-fold magnification, the crystal deposit formed on the sieve on pumping through eight 250 ml batches of the spray liquor according to Example (A).
Figure 2:
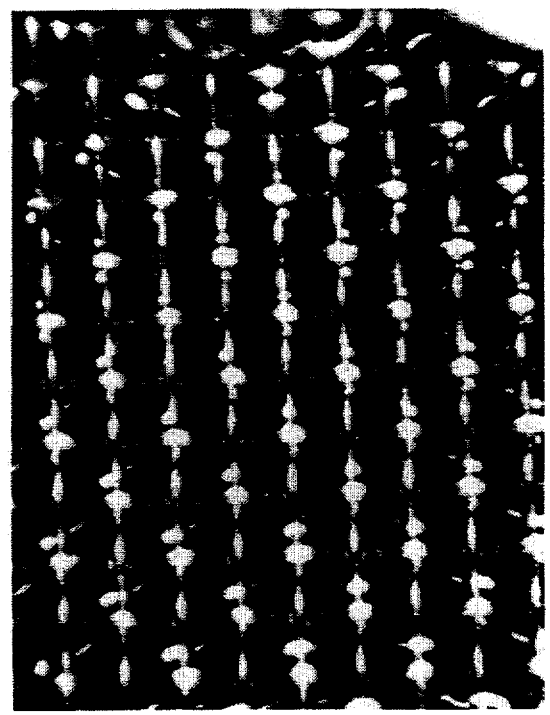
FIG. 2 shows, in 25-fold magnification, the crystal deposit formed on the sieve on pumping through eight 250 ml batches of the spray liquor according to Example (1).
Figure 3:
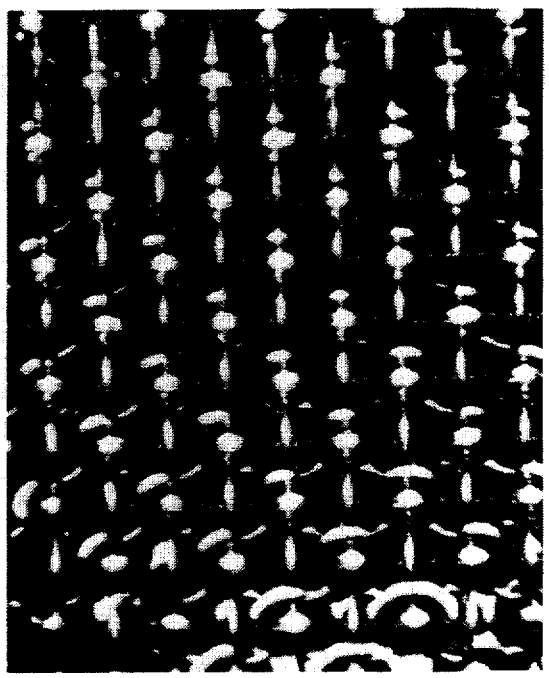
FIG. 3 shows, in 25-fold magnification, the crystal deposit formed on the sieve on pumping through eight 250 ml batches of the spray liquor according to Example (2).
Figure 4:
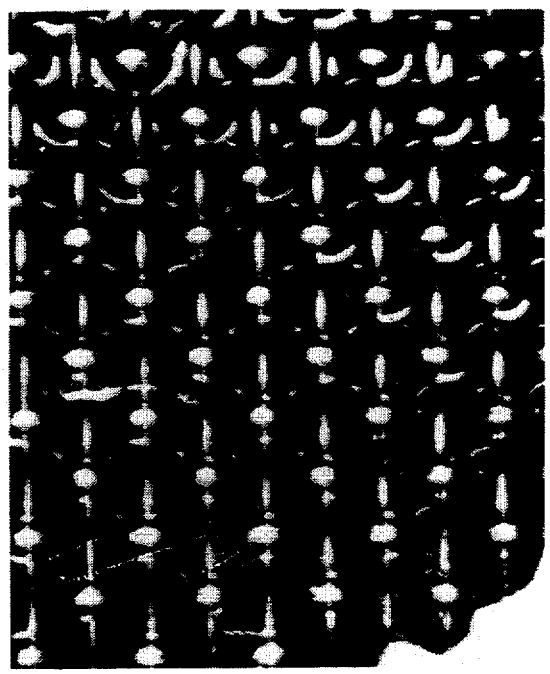
FIG. 4 shows, in 25-fold magnification, the crystal deposit formed on the sieve on pumping through eight 250 ml batches of the spray liquor according to Example (3).

The figures show that the sieve is partly blocked in the case of the known spray liquor according to Example (A), whereas in the case of the spray liquors according to Examples (1) to (3), no crystal deposit is observed.

It is understood that the specification and examples are illustrative but not limitative of the present invention and that other embodiments within the spirit and scope of the invention will suggest themselves to those skilled in the art.

We claim:
1. An aqueous spray liquor composition comprising
a) at least one component selected from the group consisting of 1-(4-chlorophenyl)-4,4-dimethyl-3-(1,2,4-triazol-1-yl-methyl)-pentan-3-ol of the formula

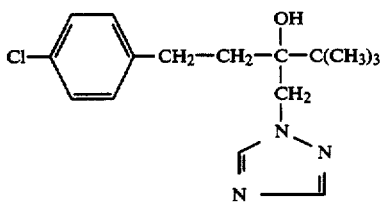

(II)

and 1-(4-chlorophenoxy)-3,3-dimethyl-1-(1,2,4-triazol-1-yl)-butan-2-ol of the formula

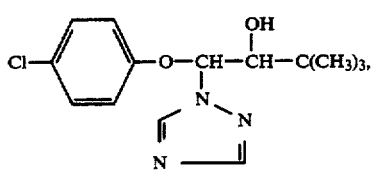
(III)

and b) at least one N-alkyl-lactam of the formula

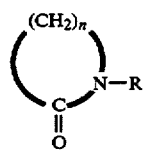
(I)

in which

R represents alkyl having 8 to 18 carbon atoms and n represents the numbers 3, 4, or 5, and optionally at least one member selected from the group consisting of a surface-active agent, organic diluent and low temperature stabilizer and wherein the active compounds II plus III are present in an amount of from about 0.0001 to 3 per cent by weight and the ratio of compounds II plus III:I is from about 1:0.2 to 1:5.

2. A composition according to claim 1, wherein in the N-alkyl lactam R represents alkyl having 8 to 14 carbon atoms.

3. A composition according to claim 1, wherein in the N-alkyl lactam R represents alkyl having 8, 10 or 12 carbon atoms.

4. A composition according to claim 1, wherein the N-alkyl lactam is N-(n-dodecyl)-caprolactam.

5. A composition according to claim 1, wherein the N-alkyl lactam is N-(n-octyl)-pyrrolidone.

6. A composition according to claim 1, wherein the N-alkyl lactam is N-(n-dodecyl)-pyrrolidone.

7. A composition according to claim 1, wherein the N-alkyl lactam is a mixture of N-(n-octyl)-pyrrolidone and N-(n-docecyl)-pyrrolidone.

8. A composition according to claim 1, further including a diluent selected from the group consisting of methyl isobutyl ketone, cyclohexanone, dimethylformamide, N-methyl-pyrrolidone, butyrolactone, dimethyl sulphoxide, xylene, propylene glycol monomethyl ether-acetate, dibutyl adipate, hexyl acetate, heptyl acetate, tri-n-butyl citrate, di-n-butyl phthalate, ethanol, n-and i-propanol, n- and i-butanol, n- and i-amyl alcohol, benzyl alcohol and 1-methoxy-2-propanol.

9. A composition according to claim 1, further including N-methyl-pyrrolidone as a diluent.

10. A method of controlling crystal growth in an aqueous spray liquor comprising at least one component selected from the group consisting of 1-(4-chlorophenyl)-4,4-dimethyl-3-(1,2,4-triazol-1-yl-methyl)-pentan-3-ol and 1-(4,chlorophenoxy)-3,3-dimethyl-1-(1,2,4-triazol-1-yl)-butan-2-ol, comprising adding to the aqueous spray liquor a crystallization-inhibiting effective amount of an N-alkyl-lactam of the formula

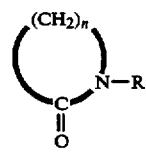
(I)

in which

R represents alkyl having 8 to 18 carbon atoms and n represents the numbers 3, 4 or 5.

* * * * *

UNITED STATES PATENT AND TRADEMARK OFFICE
CERTIFICATE OF CORRECTION

PATENT NO. : 5,369,118
DATED : November 29, 1994
INVENTOR(S) : Reizlein et al.

It is certified that error appears in the above-indentified patent and that said Letters Patent is hereby corrected as shown below:

Col. 1, line 43

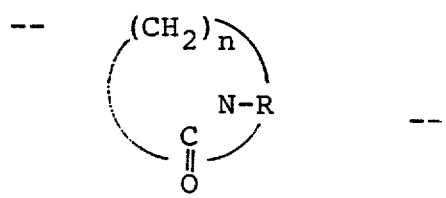

Delete " ... " and substitute -- ... --

Signed and Sealed this

Fourteenth Day of March, 1995

Attest:

BRUCE LEHMAN

Attesting Officer     Commissioner of Patents and Trademarks